(12) United States Patent
Kornet et al.

(10) Patent No.: US 8,437,850 B2
(45) Date of Patent: May 7, 2013

(54) AUTOMATIC ENABLING OF POST LONG PAUSE OVERDRIVE PACING

(75) Inventors: Lilian Kornet, Maastricht (NL); Roger Kessels, Sittard (NL)

(73) Assignee: Medtronic, Inc., Minneapolis, MN (US)

( * ) Notice: Subject to any disclaimer, the term of this patent is extended or adjusted under 35 U.S.C. 154(b) by 1132 days.

(21) Appl. No.: 11/679,330

(22) Filed: Feb. 27, 2007

(65) Prior Publication Data

US 2007/0270913 A1    Nov. 22, 2007

Related U.S. Application Data

(63) Continuation-in-part of application No. 11/554,727, filed on Oct. 31, 2006, now Pat. No. 7,729, 763.

(60) Provisional application No. 60/747,627, filed on May 18, 2006.

(51) Int. Cl.
*A61N 1/00* (2006.01)
*A61B 5/04* (2006.01)

(52) U.S. Cl.
USPC .............. 607/14; 607/17; 607/119; 600/509; 600/515

(58) Field of Classification Search .............. 607/14, 607/17, 119; 600/509, 515
See application file for complete search history.

(56) References Cited

U.S. PATENT DOCUMENTS

| | | | |
|---|---|---|---|
| 5,713,929 A | 2/1998 | Hess et al. | |
| 5,978,709 A | 11/1999 | Begemann | |
| 6,058,328 A | 5/2000 | Levine et al. | |
| 6,292,694 B1 | 9/2001 | Schloss et al. | |
| 6,411,847 B1 | 6/2002 | Mower | |
| 6,813,516 B2 | 11/2004 | Ujhelyi et al. | |
| 7,127,292 B2 | 10/2006 | Warman et al. | |
| 2002/0099414 A1 | 7/2002 | Evers et al. | |
| 2003/0144698 A1* | 7/2003 | Ujhelyi et al. | 607/4 |
| 2003/0204211 A1* | 10/2003 | Condie et al. | 607/17 |
| 2004/0088010 A1* | 5/2004 | Warman et al. | 607/5 |
| 2004/0171959 A1* | 9/2004 | Stadler et al. | 600/518 |

OTHER PUBLICATIONS

Adler et al. "Efficacy of Pacing Therapies for Treating Atrial Tachyarrhythmias in Patients with Ventricular Arrhythmias Receiving a Dual-Chamber Implantable Cardioverter Defibrillator" Circulation 200; 104; pp. 887-892.*

* cited by examiner

*Primary Examiner* — Nicole F Lavert
(74) *Attorney, Agent, or Firm* — Reed A. Duthler; Stephen W. Bauer

(57) ABSTRACT

A method and apparatus for controlling an atrial overdrive pacing therapy include detecting an atrial arrhythmia episode and determining if the atrial arrhythmia episode is an early recurring episode. Delivery of the atrial overdrive pacing therapy is enabled in response to the early recurring episode and commences upon detection of an atrial arrhythmia episode or a long pause.

24 Claims, 6 Drawing Sheets

AUTOMATIC ENABLING OF POST LONG PAUSE OVERDRIVE PACING

CROSS REFERENCE TO RELATED APPLICATION

The present non-provisional U.S. patent application is a continuation-in-part of prior non-provisional patent application entitled "POST LONG PAUSE OVERDRIVE PACING IN RESPONSE TO ATRIAL TACHYARRHYTHMIA EPISODE", filed on Oct. 31, 2006 having application Ser. No. 11/554,727, no U.S. Pat. No. 7,729,763 issued on Jun. 1, 2010 and claims the benefit of prior provisional patent application having a common title which was filed on 18 May 2006 and is identified as application Ser. No. 60/747,627.

FIELD OF THE INVENTION

The present invention relates to the field of diagnostics, monitoring and therapy delivery by implantable medical devices (IMDs) for patients experiencing atrial arrhythmia episodes, such as flutter, fibrillation, and the like.

BACKGROUND OF THE INVENTION

Some heart patients experience episodes of atrial tachyarrhythmia, including atrial fibrillation and/or atrial flutter (AF). AF is recognized as the primary cause of thromboembolic stroke and exacerbation of heart failure. AF causes the highest number of hospitalizations and is associated with a high mortality and impaired quality of life. In addition, atrial tachyarrhythmias beget ventricular tachyarrhythmias in some patients.

For heart patients having a multi-chamber pacemaker, AF episodes present an additional problem, in that the pacemaker may coordinate ventricular pacing with atrial activity. When an AF episode begins, it is undesirable for ventricular pacing to track the atrial rhythm. Accordingly, some pacemakers are equipped with a "mode switching" capability. The principal purpose of such mode switching is to prevent the pacing system from delivering ventricular paces that track high rate atrial activity when the atrium experiences an episode of atrial tachycardia. When the atrial rate is normal, the pacemaker assumes a tracking mode, such as DDD or DDDR, in which ventricular pacing tracks atrial activity. When an AF episode occurs, however, the pacemaker mode switches to a non-tracking pacing mode, such as DDIR, and paces the ventricle independently of atrial activity.

When an AF episode occurs, the pacemaker or another medical device may apply therapy to terminate the AF episode. Therapy may include application of a cardioversion shock or administration of drug. Another therapy for atrial tachycardia is anti-tachycardia pacing (ATP) in which a high frequency burst of stimulation pulses is delivered. ATP is often effective in disrupting an atrial arrhythmia such as AF and terminating the episode. Of course, an AF episode may also terminate spontaneously.

It has been observed that a recurrent AF episode may occur within seconds or minutes after the termination of the first, primary AF episode, and herein such an episode is referred to as an early recurring AF (ERAF) episode. Although an ERAF episode does not always follow the termination of a preceding AF episode, it has been demonstrated clinically that a patient may have an increased risk of a recurrent AF episode for a period of time following a prior AF episode, either an initial or another ERAF episode. This phenomenon has been attributed to the fact that the local refractory period after AF is temporarily shortened, causing the substrate to be vulnerable to premature atrial beats which will re-induce AF. In patients with AF, who have a pacemaker implanted, atrial overdrive pacing may influence mechanisms which are held responsible for the early recurrence of AF and thereby reduce the likelihood of ERAF episodes. Post-Mode Overdrive Pacing (PMOP) refers to the delivery of atrial overdrive pacing after termination of a pacing mode switch following termination of an AF episode, when a sinus rhythm has been restored but the tissue is still vulnerable to ERAF episodes induced, for example, by premature beats.

DETAILED DESCRIPTION

Figure 1:
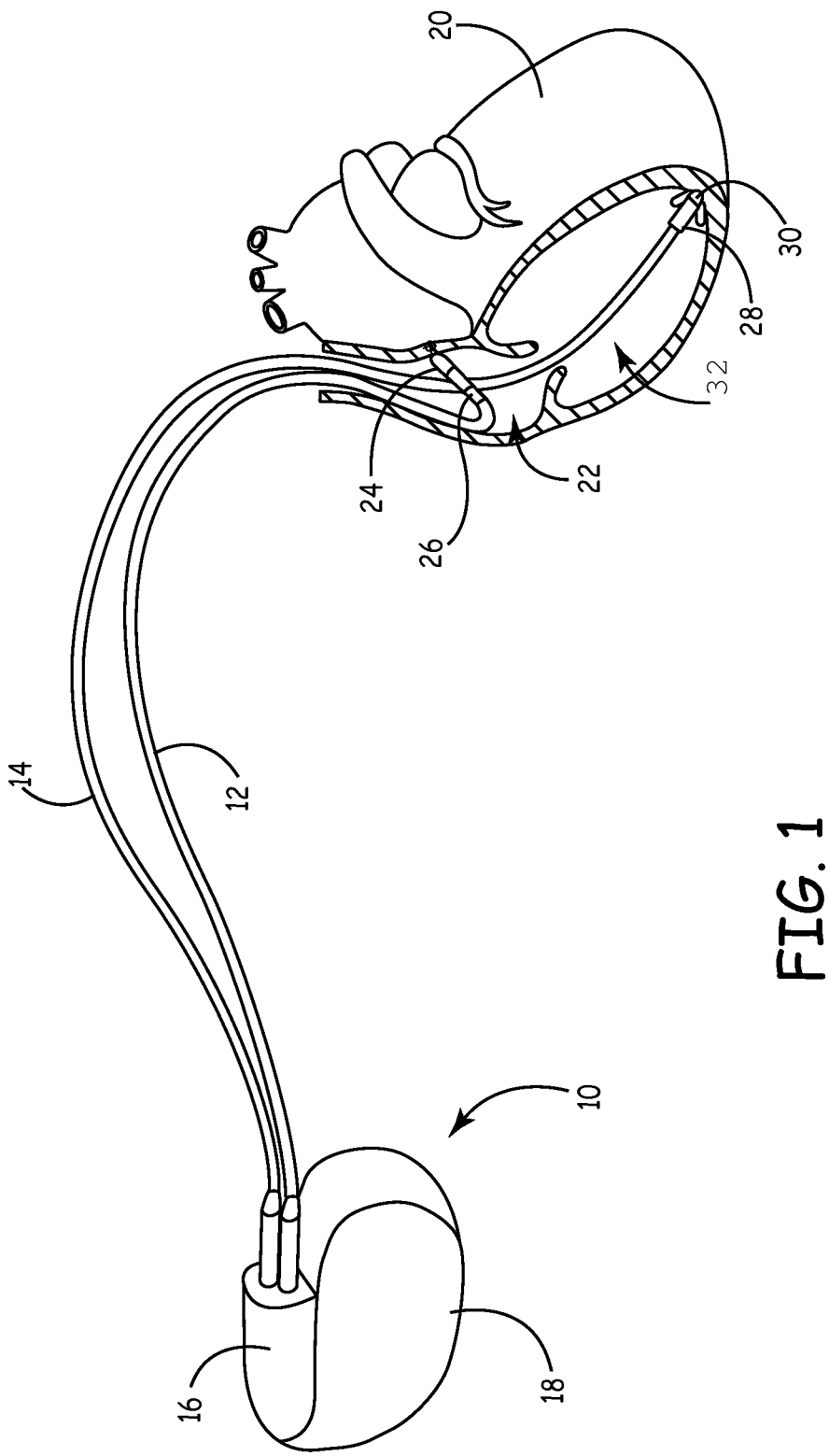
FIG. 1 is a schematic view of an implantable medical device coupled to a patient's heart.

In the following description, references are made to illustrative embodiments for carrying out the invention. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Embodiments of the invention described herein are directed toward the prevention of ERAF using atrial overdrive pacing. As will be described in detail below, atrial overdrive pacing is controlled by an IMD to commence at an earlier time following an AF detection then known PMOP algorithms so as to more effectively reduce the likelihood of ERAF. Furthermore, the delivery of such early atrial overdrive pacing is controlled by the IMD to be enabled in patients found to be most likely to experience ERAF episodes.

In past practice, overdrive pacing has been applied at the termination of a mode switch after sinus rhythm has been restored in the atria to prevent ERAF. However, some patients are at risk of experiencing ERAF following termination of an AF episode, prior to the initiation of overdrive pacing after termination of the mode switch. As such, various embodiments of the present invention provide techniques for delivering atrial overdrive pacing at a relatively earlier time following an AF episode detection rather than at termination of the mode switch. AF, as used herein, refers to any atrial arrhythmia episode characterized by a high atrial rate and detected by an implanted device according to programmed atrial arrhythmia detection criteria. Such arrhythmias may include rhythms referred to as atrial tachycardia, atrial flutter and atrial fibrillation.

As used herein "overdrive pacing" generally refers to pacing the heart at a rate slightly greater than an intrinsic rate expected during normal sinus rhythm. For example, overdrive pacing may be delivered at an interval 50 to 500 ms shorter than an intrinsic cycle length, which may be measured or expected to occur during sinus rhythm. Since techniques described herein include delivering overdrive pacing prior to confirming AF termination, i.e. prior to restoring sinus rhythm, the overdrive pacing rate may be set to a nominal or default overdrive rate that is expected to be somewhat higher than a typical sinus rate, for example 100 to 120 pulses per minute.

Overdrive pacing is not to be confused with ATP therapies which involve delivering a high frequency train of pulses, either in a burst (pulses separated by equal intervals) or in a ramp (pulses separated by decreasing intervals). The intervals between ATP pulses are set according to tachycardia intervals sensed during an AT/AF episode rather than based on a measured or expected sinus rate as in overdrive pacing. As such, ATP pulses are generally delivered at a higher rate than overdrive pacing pulses and include only a programmed number of pulses, e.g. 8-10 pulses.

Various definitions of "recurrent" with regard to arrhythmia episodes can be found among clinicians and physicians. For example, one may deem that an AF episode is "recurrent" when the episode follows within a minute of an earlier terminated episode of AF. Another physician may deem that an AF episode is "recurrent" when the episode follows within three hundred or another number of specified beats after an earlier terminated AF episode. A third physician may use "recurrent" to refer to an AF episode that follows within ten minutes or six hundred beats of an earlier terminated episode, whichever is longer.

As used herein, the term "early recurrent" is intended to encompass all such usages of the term "recurrent" as it relates to an AF episode. In other words, an ERAF episode is any AF episode that recurs within a predefined time or number of cardiac cycles after a prior AF episode termination. The predefined time or number of cardiac cycles can be defined according to physician preference. Furthermore it is recognized that an early recurrent episode may include any episode that recurs within a predefined time after a prior AF episode detection as long as an intervening termination of the prior AF episode has been confirmed. In other words, the determination of an early recurrent episode may be made based on either a detection time or a termination time of a previously occurring AF episode. According to some embodiments of the invention, historical data is used to determine when a patient is at risk of experiencing an ERAF episode, and controls the triggering of atrial overdrive pacing accordingly. In particular, the early overdrive pacing algorithm described herein, initiated in response to an AF detection or a required number of long pauses following an AF detection, can be enabled based upon a metric of ERAF episodes detected, such as the duration of ERAF episode(s), the number of ERAF episodes, the frequency, the percentage of AF episodes followed by ERAF episodes and the like, such that the overdrive pacing algorithm is activated only when particularly relevant.

FIG. 1 provides a schematic view of one embodiment of an IMD 10 that can be adapted to perform the methods described herein for controlling atrial overdrive pacing. In accordance with one embodiment of the invention, IMD 10 can be configured to apply overdrive pacing to one or both atria following detection of an AF episode and a required number and duration of relatively long pauses between successive P-waves in an effort to prevent an ERAF episode. In particular, IMD 10 is programmed to automatically deliver overdrive pacing therapy to prevent an ERAF episode. The IMD 10 is embodied as a cardiac pacemaker or implantable cardioverter-defibrillator (ICD) including pacing and sensing leads 12, 14 coupled to a connector module 16 of a hermetically sealed enclosure 18 and implanted near a heart 20 of a subject. Pacing and sensing leads 12, 14 sense electrical signals attendant to the depolarization and repolarization of the heart 20, and further provide pacing pulses for causing depolarization of cardiac tissue in the vicinity of the distal ends of the leads as needed.

Atrial pacing and sensing lead 12 extends from connector module 16 to the right atrium 22 of heart 20 and may alternatively extend to the left atrium. At least one pair of atrial electrodes 24, 26 are disposed in communication with an atrial chamber (e.g., as depicted, right atrium 22) at the distal end of atrial lead 12. Ventricular pacing and sensing lead 14 extends from connector module 16 to the right ventricle 32 of heart 20. Ventricular electrodes 28,30 are disposed in right ventricle 32 at the distal end of ventricular lead 14. Leads 12, 14 may carry one or more electrodes for use in unipolar, bipolar or multipolar configurations. Ventricular electrodes may additionally or alternatively be placed in operative relation to the left ventricle.

IMD 10 can deliver cardiac pacing therapy to a ventricle 32 via electrodes 28, 30. IMD 10 can coordinate ventricular pacing with atrial activity sensed via atrial electrodes 24, 26 during atrial tracking pacing modes. Atrial electrodes 24, 26 can also be employed to sense an atrial tachyarrhythmia such as fibrillation or flutter (AF), and to administer therapy, such as overdrive pacing. IMD 10 is configured to switch pacing modes to a non-atrial tracking mode upon detection of AF.

Overdrive pacing is administered via atrial electrodes 24, 26. Embodiments of the present invention are directed to triggering atrial overdrive pacing therapy to prevent an ERAF episode. In other embodiments, early delivery of atrial overdrive pacing may be used to try to terminate an AF episode. IMD 10 regulates overdrive pacing control parameters including the rate and duration of overdrive pacing. IMD 10 is further configured to determine when to enable automatic triggering of atrial overdrive pacing and to detect triggering conditions.

Figure 2:
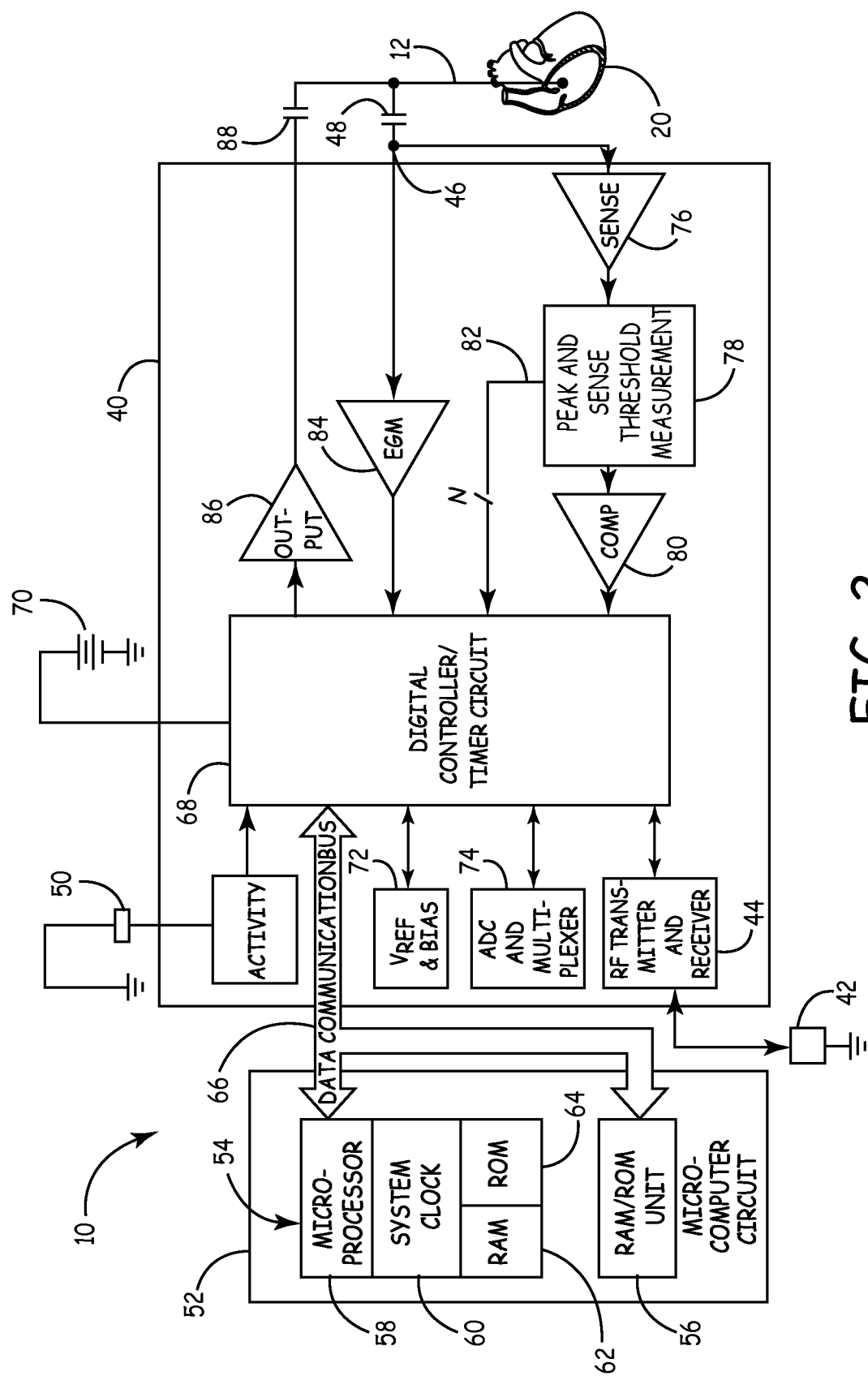
FIG. 2 is a block diagram illustrating the constituent components of an implantable medical device such as the implantable medical device in FIG. 1.

FIG. 2 shows a block diagram illustrating the constituent components of an IMD 10 in accordance with one embodiment of the invention, in which IMD 10 is a pacemaker having a microprocessor-based architecture. IMD 10 is programmable and may be programmed with an external programming unit (not shown in the figures). The programmer may provide a series of encoded signals to IMD 10 via wireless telemetry. An input/output circuit 40 may be coupled to an antenna 42 to permit uplink/downlink telemetry through an RF transmitter and receiver telemetry unit 44. Telemetry unit 44 receives programming instructions, including instructions and control parameter values for controlling atrial overdrive pacing. Programming data includes default overdrive pacing parameters, one or more overdrive pacing triggers and other overdrive pacing parameters/instructions as will be described below. Telemetry unit 44 is also used to transmit or receive information, such as data stored by IMD 10, during device interrogations. Historical data concerning AF episodes collected by IMD 10 and/or the number and/or length of long pauses used to trigger overdrive pacing may be transmitted by IMD 10 during an interrogation session. Any of a number of programming and telemetry methodologies may be employed to transmit information to and receive information from IMD 10.

Atrial lead 12 and ventricular lead 14 (not shown in FIG. 2) are coupled to input/output circuit 40. For simplicity, IMD 10 in FIG. 2 is shown with atrial lead 12 connected thereto, but similar circuitry and connections not explicitly shown in FIG. 2 may apply to ventricular lead 14. Lead 12 is coupled to node 46 in IMD 10 through input capacitor 48. Input/output circuit 40 delivers pacing stimuli to the atrium as will be described in more detail below.

Input/output circuit 40 may further receive input from an activity sensor 50, such as a piezoceramic accelerometer bonded to a hybrid circuit located inside enclosure 18 (shown in FIG. 1). Activity sensor 50 typically (although not necessarily) provides a sensor output that varies as a function of a measured parameter relating to a patient's metabolic requirements.

IMD 10 includes a microcomputer circuit 52. Microcomputer circuit 52 stores and executes software-implemented algorithms for detecting and responding to arrhythmias such as AF. In some embodiments of the invention, IMD 10 may be programmed to operate in various rate-responsive or non-rate-responsive modes. In addition, microcomputer circuit 52 stores and executes software-implemented algorithms for managing overdrive pacing parameters according to the techniques of the invention, and for controlling delivery of overdrive pacing therapy according to the overdrive pacing parameters.

Microcomputer circuit 52 may include an on-board circuit 54 and off-board circuit 56. On-board circuit 54 includes microprocessor 58, system clock circuit 60 and on-board random-access memory (RAM) 62 and read-only memory (ROM) 64. Off-board circuit 56 comprises a RAM/ROM unit. On-board circuit 54 and off-board circuit 56 are each coupled by a data communication bus 66 to digital controller/timer circuit 68. Microcomputer circuit 52 may comprise a custom integrated circuit device augmented by standard RAM/ROM components. Memory 56, 62 or 64 store overdrive pacing control parameters, and may store data pertaining to the evaluation and efficacy of overdrive pacing therapy, as will be described below. Other information stored may include counter values or other data relating to early overdrive pacing triggering criteria being met, overdrive pacing deactivated by an on-going episode of atrial tachycardia, overdrive pacing deactivated due to a newly-detected atrial tachycardia and the like.

Electrical components shown in FIG. 2 are powered by an implantable battery power source 70. For the sake of clarity, the coupling of battery power source 70 to the various components of IMD 10 is not shown in the FIG. 2. VREF and bias circuit 72 generates stable voltage reference and bias currents for analog circuits included in input/output circuit 40. Analog-to-digital converter (ADC) and multiplexer unit 74 digitizes analog signals and voltages for digital processing.

Operating commands for controlling the timing of electrical stimulations delivered to heart 20 by IMD 10 are coupled from microprocessor 58 via data bus 66 to digital controller/timer circuit 68, where digital timers and counters establish the various refractory, blanking and other timing windows used in the detection of cardiac activity and the delivery of electrical stimulations.

Sensing circuitry coupled to digital controller/timer circuit 68 detects cardiac activity. Cardiac signals detected via lead 12 are processed by sensing circuitry, which includes sense amplifier 76, peak sense and threshold measurement unit 78 and comparator/threshold detector 80. In general, sense amplifier 76, peak sense and threshold measurement unit 78 and comparator/threshold detector 80 cooperate to sense the occurrence and timing of cardiac events such as atrial depolarizations. Sense amplifier 76 amplifies sensed electrical cardiac signals and provides an amplified signal to peak sense and threshold measurement unit 78, which in turn provides an indication of peak sensed voltages and measured sense amplifier threshold voltages on multiple conductor signal path 82 to digital controller/timer circuit 68. An amplified sense amplifier signal is also provided to comparator/threshold detector 80.

Cardiac signals detected via lead 12 may also be received by electrogram (EGM) amplifier 84. In general, the electrogram signal supplied by EGM amplifier 84 preserves the morphology of the cardiac signal. Digital controller/timer circuit 68 may process the electrogram signal supplied by EGM amplifier 84, and may transmit the electrogram signal to an external programmer for observation and analysis by a physician.

Output pulse generator 86 provides pacing stimuli to heart 20 through coupling capacitor 88 in response to a pacing trigger signal provided by digital controller/timer circuit 68. The conditions that trigger generation of a pacing trigger signal may vary from patient to patient, and the conditions that may trigger generation of an atrial pacing trigger signal need not be the same as the conditions that trigger generation of a ventricular pacing trigger signal. In one embodiment of the invention, digital controller/timer circuit 68 generates atrial pacing trigger signals that cause overdrive pacing of the atrium to terminate an AF episode or to prevent a recurrent AF episode from occurring.

The invention is not limited to application with IMD 10 as depicted in FIGS. 1 and 2. The techniques of the invention may be practiced by, for example, in single-chamber pacemakers or multi-chamber pacemakers or ICDs. The invention may be practiced by devices that provide a variety of pacing, cardioversion and defibrillation therapies having various system architectures.

Devices that perform overdrive pacing of the atrium supply pacing stimuli to the atrium at a rate exceeding an intrinsic rate, called the "overdrive rate." The overdrive rate may be expressed as the number of paces supplied per unit time during overdrive pacing, as determined by the time interval between two overdrive pacing pulses. In addition, devices that perform overdrive pacing of the atrium supply pacing stimuli at the overdrive rate for a duration of time, called the "overdrive duration." The overdrive rate and overdrive duration are two overdrive pacing parameters, but not the only parameters pertaining to controlling overdrive pacing. Other overdrive pacing control parameters will be described below.

Figure 3:
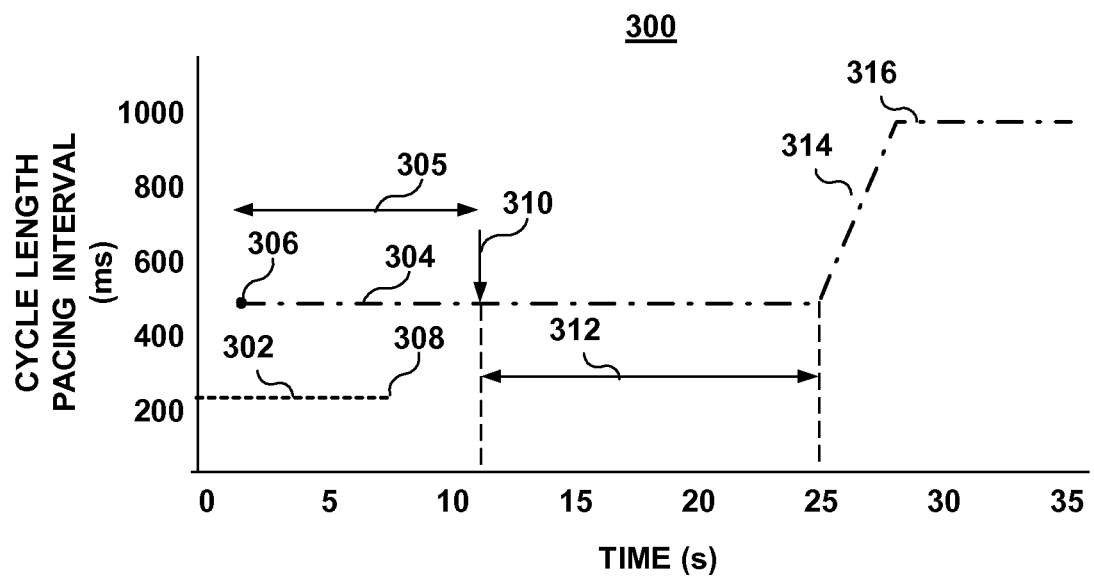
FIG. 3 is a timing diagram illustrating one method for delivering atrial overdrive pacing.

FIG. 3 is a timing diagram 300 illustrating one method for delivering atrial overdrive pacing. The timing diagram 300 illustrates an AF episode 302 detected at 0 seconds having a cycle length interval of approximately 250 ms (equal to 240 beats per minute). According to one embodiment, atrial overdrive pacing 304 is initiated at 306 at a time soon after AF detection. The atrial overdrive pacing rate may be based on sensed atrial rate occurring prior to the AF detection or may be set to a default overdrive rate, for example 120 pulses per minute corresponding to a pacing interval of 500 ms. In contrast to post-mode switch atrial overdrive pacing, the atrial overdrive pacing 304 is initiated during the AF episode in an attempt to terminate the AF.

After a short interval of time 305 (for example 10 ventricular beats or 10 seconds), the device determines if AF is still present. If AF is re-detected, i.e. the AF episode is sustained, overdrive pacing would be de-activated at 310. If the AF episode is no longer detected at 310, overdrive pacing 308 continues at the overdrive rate and for a programmed duration 312. In the example shown in FIG. 3, the AF episode 302 is terminated at 308. As such, the device would not detect AF at 310 and continue delivering overdrive pacing 304 for a programmed duration 312. In contrast to anti-tachycardia pacing techniques used for AF termination, the overdrive pacing 304 may continue for a period of time after detecting AF termination 308.

Upon expiration of the programmed overdrive pacing duration 312, the overdrive pacing interval increases relatively rapidly (e.g., within approximately three seconds) to a programmed base rate 316 (e.g. 60 pulses per minute or 1000 ms pacing interval). Lower rate pacing may continue at the base rate 316 unless an intrinsic rate greater than the programmed lower rate emerges.

While the overdrive pacing duration 312 is shown relative to the time 310 for determining if AF is still detected, it is recognized that in some embodiments, the device may be capable of monitoring for AF termination throughout overdrive pacing without interrupting overdrive pacing. As such, if AF termination 308 is detected within a predetermined interval after the onset 306 of overdrive pacing, a programmed overdrive duration 312 may commence upon detecting AF termination 308. If detection of AF requires a pause in overdrive pacing to allow accurate sensing of intrinsic atrial signals, the overdrive duration 312 may be defined relative to the time point 310 at which the device determines if the AF episode 302 is no longer being detected.

Figure 4:
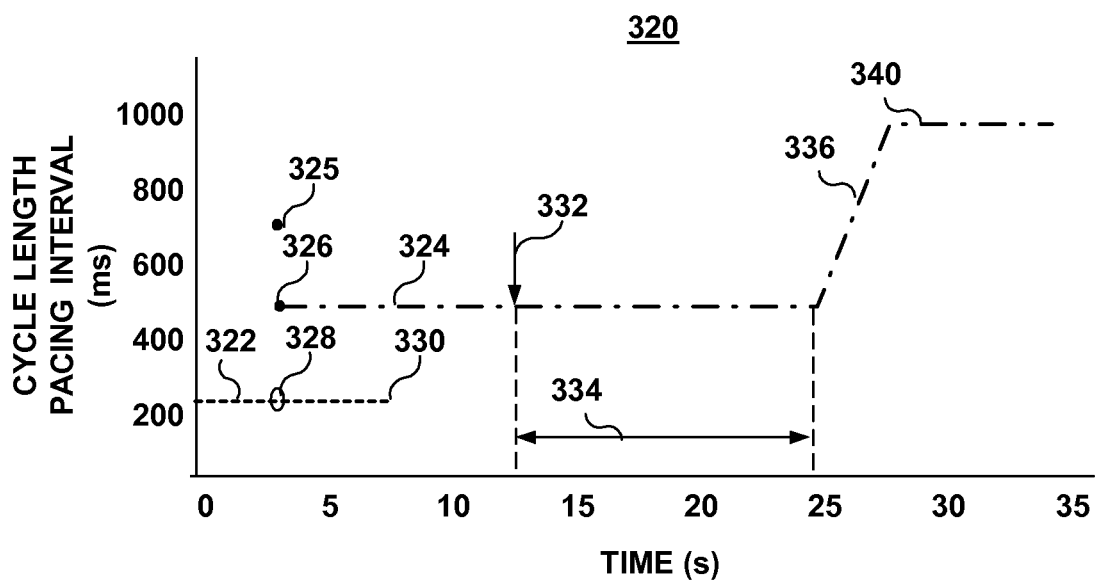
FIG. 4 is a time line illustrating an alternative method for delivering atrial overdrive pacing.

FIG. 4 is a time line illustrating an alternative method 320 for delivering atrial overdrive pacing. In this embodiment, an AF episode 322 is detected at 0 seconds. After detecting AF, the device begins monitoring for a long pause between consecutive atrial depolarizations. A long pause is generally defined as an atrial cycle length that is longer than the maximum atrial arrhythmia detection interval. As such, an atrial cycle length criteria for detection a long pause may be a programmable parameter. A long pause 328 is shown during the AF episode 322 corresponding to an atrial cycle 325 having a cycle length of approximately 700 ms. According to one embodiment of the invention, atrial overdrive pacing 324 commences after detection a required number of long pauses exceeding a predefined minimum cycle length interval. For example, in the method 320, atrial overdrive pacing 324 commences immediately following a long pause 328, which occurs after detection of AF episode 322 and prior to detecting AF termination 330 by the IMD. The overdrive pacing interval may be longer or shorter than the detected long pause and may be nominally defined or defined as a function of the long pause cycle length.

AF termination detection 330 by the IMD typically requires sensing of a predetermined number of sinus intervals, for example 5 sinus intervals. Thus the time of AF termination as detected by the IMD somewhat lags the actual time of AF termination. In past practice, post-mode switch overdrive pacing or PMOP has been initiated after termination of a pacing mode switch, which occurs after device-detected AF termination. A long pause generally occurs upon "actual" AF termination, prior to the time of device-determined AF termination. By initiating overdrive pacing upon sensing a long pause, which is associated with actual AF termination rather than the device-detected AF termination, overdrive pacing is initiated earlier than in past techniques.

Under some circumstances a long pause detection interval may be programmed to be longer than an intrinsic rhythm. As such, a long pause might be detected after "device-determined" termination. As such, if a long pause is sensed after the device detects AF termination according to termination detection requirements, and overdrive pacing has not already been initiated, overdrive pacing may be triggered by a long pause sensed after device-determined AF termination in some embodiments.

A long pause may be detected during an AF episode due to undersensing in which case the overdrive pacing may be initiated prior to actual AF determination. As such, after a short time interval (for example 10 ventricular beats or 10 seconds) the device re-determines at 332 if AF is still present or has been terminated. If AF is re-detected, i.e. the presently detected AF episode is sustained, overdrive pacing is terminated. The long pause that triggered the overdrive pacing was likely due to undersensing rather than actual AF termination. If the AF episode 322 has terminated, as indicated at 330, overdrive pacing 324 continues for a programmed duration 334 and rate. The method 320 shown in FIG. 4 illustrates one possible use of atrial overdrive pacing initiated after AF detection and subsequent to one or more long pauses for preventing an ERAF episode. The overdrive pacing interval is rapidly increased at 336 to a base pacing rate 340 after the programmed overdrive pacing duration 334. Lower rate pacing may continue at the base rate 340 until a higher intrinsic rate emerges.

While the overdrive pacing duration after determining that the AF episode is detected is shown to be on the order of 15 to 20 seconds in the timing diagrams of FIGS. 3 and 4, it is recognized that other durations may be implemented. For example, overdrive pacing may be delivered for 1 minute, 5 minutes, 10 minutes or other programmed durations for reducing the likelihood of an ERAF episode.

Figure 5:
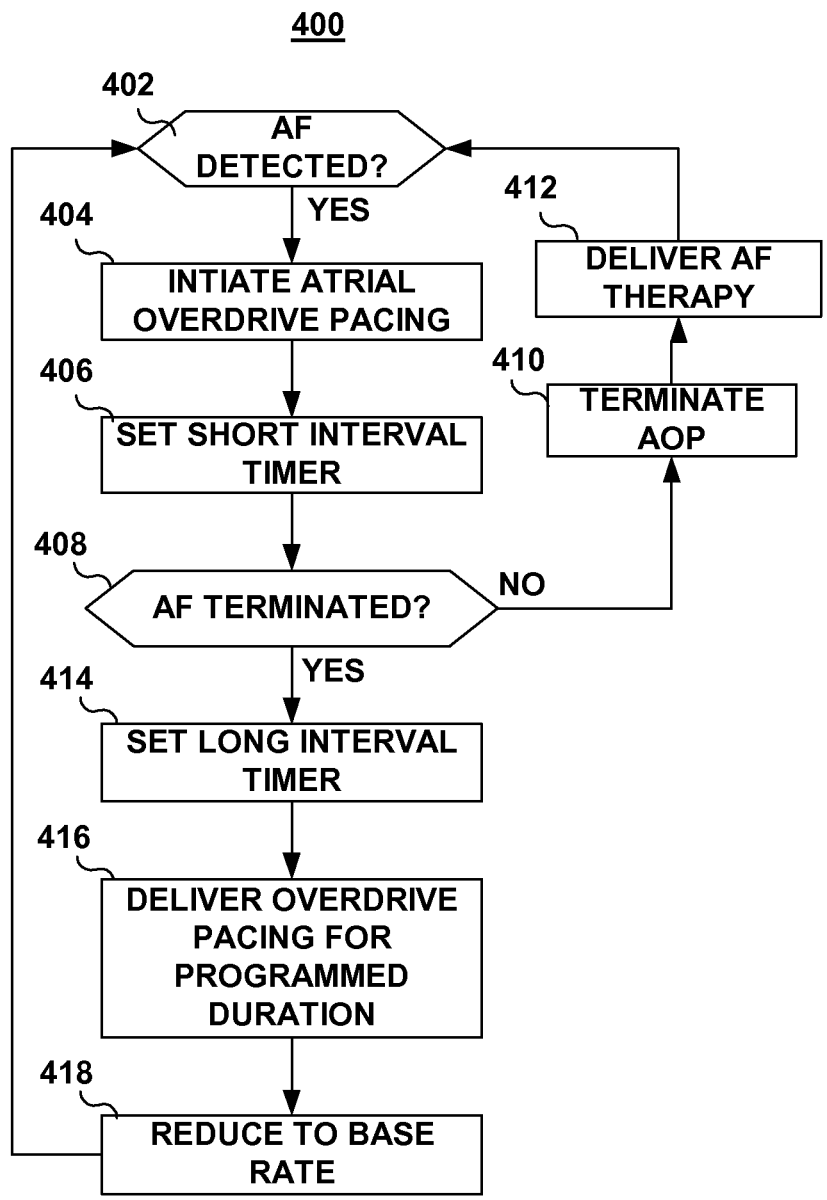
FIG. 5 is a flow chart of one method for controlling atrial overdrive pacing in an IMD.

FIG. 5 is a flow chart of one method 400 for controlling atrial overdrive pacing in an IMD. The method 400 includes the salient steps for controlling atrial overdrive pacing according to one embodiment of the invention, corresponding generally to the timing diagram shown in FIG. 3. Flow chart 400, and other flow charts presented herein, are intended to illustrate the functional operation of the device, and should not be construed as reflective of a specific form of software or hardware necessary to practice the invention. It is believed that the particular form of software will be determined primarily by the particular system architecture employed in the device and by the particular detection and therapy delivery methodologies employed by the device. Providing software to accomplish the present invention in the context of any modern IMD, given the disclosure herein, is within the abilities of one having skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

An AF episode is detected at 402 and overdrive pacing is activated at 404. At 406 a short interval timer is set. Upon expiration of the short interval timer, the IMD determines if AF has been terminated as indicated at block 408. If the AF episode is still present, i.e. actual AF termination has not occurred, the atrial overdrive pacing is terminated at block 410. An AF therapy, e.g. anti-tachycardia pacing or a cardioversion shock, may be delivered at block 412.

If the AF episode is terminated after the short interval, a longer interval timer is set at block 414 corresponding to a desired atrial overdrive pacing duration. In one embodiment, the short interval timer corresponds to approximately 10 seconds and the long interval timer corresponds to approximately 10 minutes. The overdrive pacing is delivered at a default programmed overdrive pacing rate, or at a rate set incrementally higher than an intrinsically sensed rate, until the long time interval expires at block 416. The pacing rate is then adjusted to a programmed base pacing rate at block 418. It is recognized that if AF is detected at any time during overdrive pacing, the overdrive pacing may be terminated and an ATP or cardioversion/defibrillation therapy may be delivered.

Figure 6:
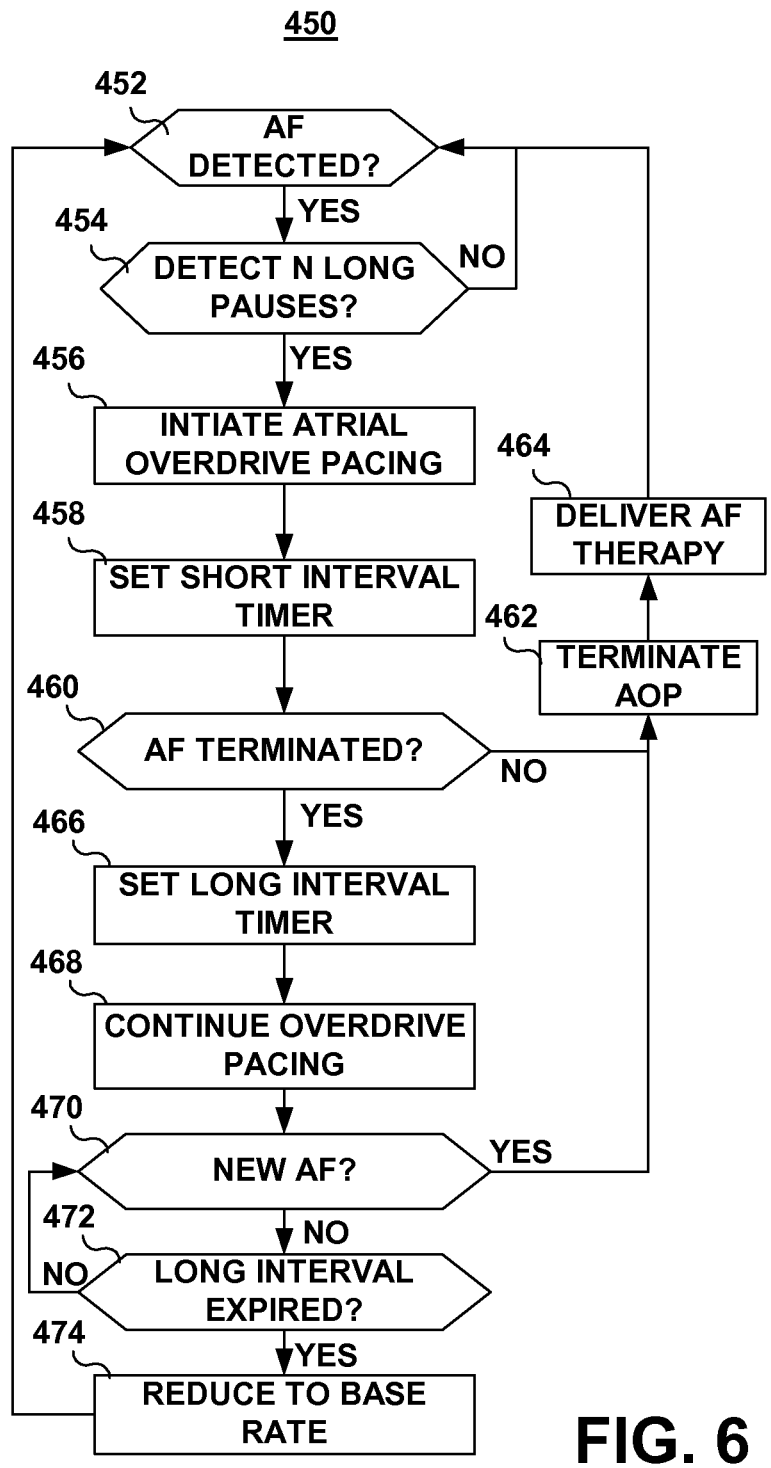
FIG. 6 is a flow chart of an alternative method for controlling atrial overdrive pacing.

FIG. 6 is a flow chart of an alternative method for controlling atrial overdrive pacing. Method 450 generally corresponds to the method illustrated by the time line shown in FIG. 4. At block 452, an AF episode is detected. After detecting AF, a sensor disposed in communication with one or both atria is operatively implemented to detect the amount of time elapsed between successive atrial depolarizations (P-waves) that includes criteria for determining when a relatively long pause between the successive P-waves occurs. Criteria for determining when a long pause occurs includes a predetermined minimum atrial cycle interval, which may correspond to the maximum atrial arrhythmia detection interval, or a predetermined increase over a previous interval(s). Prior to detecting a long pause, ATP therapy could be delivered for treating the AF episode.

Upon detecting a predetermined required number of long pauses, as indicated at block 454, atrial overdrive pacing is initiated at block 456. Any pending or scheduled ATP therapy is disabled such that ATP therapy and overdrive pacing are not delivered concomitantly. The short interval timer is set to a predetermined relatively short interval (e.g., 5 to about approximately 15 seconds) at block 458. Upon expiration of the short interval timer, the device determines if AF has been terminated at block 460, as evidenced by sensing a required number of sinus intervals for example. If AF is still present, i.e. not terminated, the atrial overdrive pacing is terminated at block 462 and an AF therapy may be delivered at block 464. One or more of the long pauses that triggered overdrive pacing may have been detected due to undersensing rather than being a long pause associated with actual AF termination. The method 450 then proceeds to step 452 with periodic, or continuous monitoring for AF.

If the AF episode is determined to be terminated at block 460, a long interval timer is set at block 466. Overdrive pacing continues at block 468 while continually or periodically monitoring for a new AF episode. If a new AF episode is detected at block 470, method 450 proceeds to block 462 to terminate the atrial overdrive pacing. An AF therapy may be delivered at block 464.

If no new AF episodes are detected, overdrive pacing continues until the long interval timer expires, i.e. for the programmed overdrive pacing duration. The pacing rate is then reduced to a programmed base rate at block 474 after expiration of the long interval (block 472). Method 450 then returns to block 452 to continue monitoring for new AF episodes.

In past practice, the pacemaker typically does not abruptly commence pacing at an overdrive pacing rate but rather gradually ramps up to a programmed overdrive pacing rate after termination of a pacing mode switch and over a transition interval wherein the rate is incrementally increased to the overdrive pacing rate. It should be noted that according to certain embodiments of the invention, a pacemaker can deliver pacing therapy to one or both atria commencing immediately at an overdrive pacing rate upon meeting overdrive pacing triggering criteria, e.g. sensing a required number of long pauses having a predefined cycle length duration.

Figure 7:
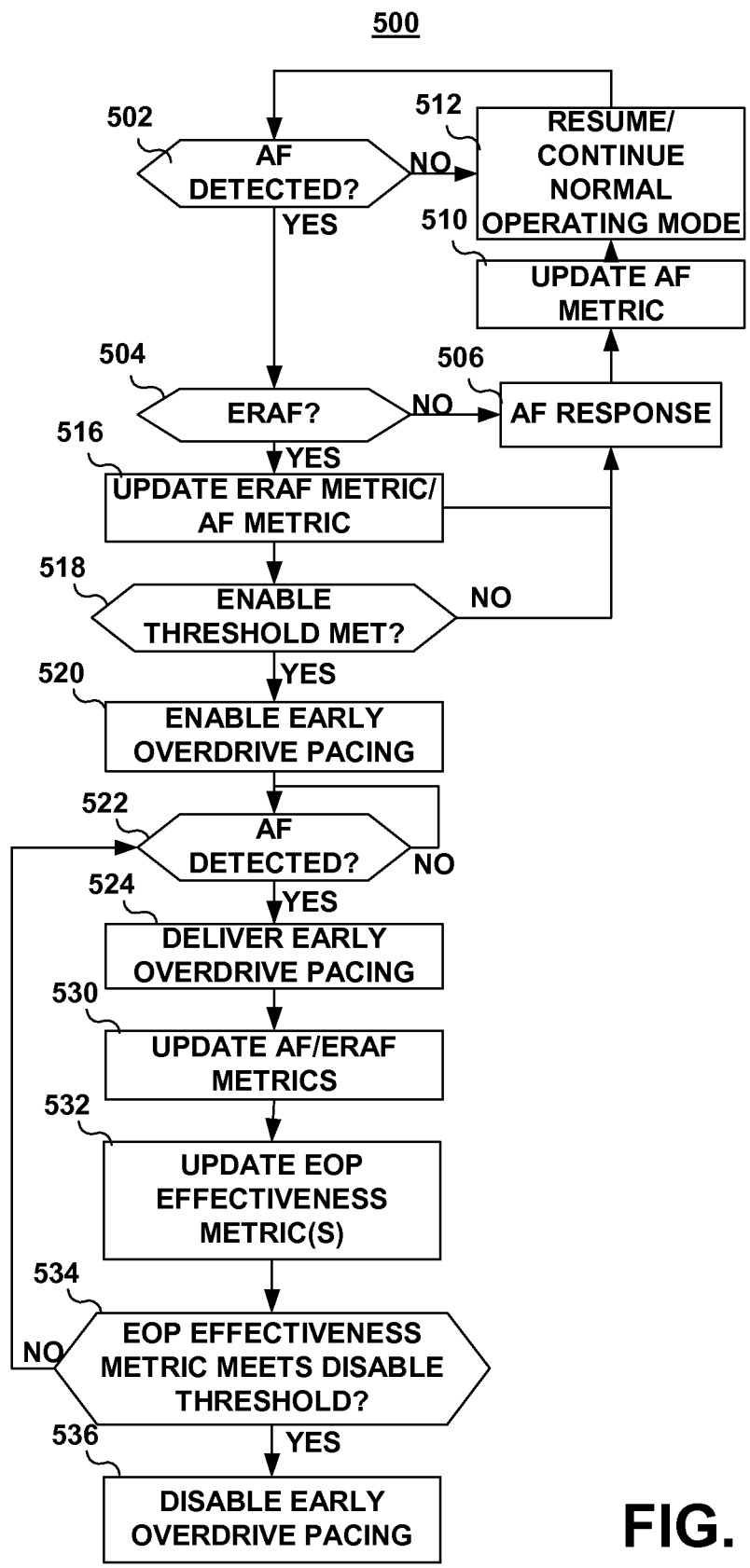
FIG. 7 is a flow chart of a method for controlling overdrive pacing based on an index or metric of ERAF episodes.

FIG. 7 is a flow chart of a method for controlling overdrive pacing based on an index or metric of ERAF episodes. At block 520, the IMD determines if AF is detected. At block 504, the IMD determines if the AF detection is within a predetermined time or number of cardiac cycles since a previously terminated AF episode. In other words, the IMD determines if the AF detection is an ERAF according to a defined early recurrence condition. If the AF detection does not correspond to an ERAF, the IMD responds to the AF detection at block 506 according to normal programmed operations. For example, the AF response provided at block 506 may include a pacing mode switch, ATP therapies, and/or an atrial cardioversion shock. The AF response at block 506 initially provided in response to a detected AF episode that is not an ERAF does not include enabling early atrial overdrive pacing algorithm.

Following the AF response, an AF metric is updated at block 510. For an example, an AF metric may be an AF burden measured as the summed durations of all detected AF episodes occurring over a measurement period, e.g., over a 24-hour period. Additionally or alternatively, the AF metric may include determining the frequency of AF detections, the mean duration of AF episodes or another measure of the occurrence of AF. At block 512, the IMD resumes or continues a normal operating mode and continues to monitor for AF at block 502.

If a detected AF episode is determined to be an ERAF at decision block 504, a metric of ERAF episodes is updated at block 516. The ERAF metric may be analogous to the AF metric but defined for specifically tracking ERAF episodes rather than all AF episodes. For example, the ERAF metric may be an ERAF burden such that the IMD is able to determine what proportion of the total AF burden corresponds to ERAF episodes. As such, an AF metric that includes all occurrences of AF, ERAF and non-ERAF episodes, may also be updated at block 516. The ERAF metric may alternatively be a count of the number of ERAF episodes detected or a percentage of AF episodes followed by an ERAF. Other ERAF metrics may be defined as a frequency of occurrences of ERAF episodes in a patient or some other measure of ERAF episodes.

The ERAF metric is used as an indication of the likelihood that the patient will experience ERAF episodes again in the future. At block 518, the IMD determines if an early overdrive pacing enable threshold has been met. The enable threshold is a threshold defined as a function of the ERAF metric. The enable threshold is used for enabling an early overdrive pacing response in patients that may benefit most from the application of early overdrive pacing, i.e. patients prone to ERAF episodes. The enable threshold may thus be defined as some level of ERAF burden, a ratio or percentage of the ERAF burden to the total AF burden, a frequency of ERAF, a percentage of the AF episodes followed by ERAF, etc.

If the enable threshold is not met, the default AF response is provided at block 506 as described previously. If the enable threshold is met at block 518, early atrial overdrive pacing therapy is enabled at block 520. Overdrive pacing may be delivered immediately in response to the currently detected ERAF. As described previously, overdrive pacing may be delivered after detecting the ERAF or after sensing a required number of long pauses. After enabling early overdrive pacing, overdrive pacing is initiated at block 524 whenever trigger criteria (e.g. required number of long pauses) have been met following any subsequently detected AF episode at block 522. The AF and ERAF metrics may continue to be updated at block 530 for use in monitoring the effectiveness of the early overdrive pacing in preventing ERAF in a given patient.

Additionally, an early overdrive pacing (EOP) effectiveness metric may be updated at block 532. The EOP effectiveness metric is used to monitor the effectiveness of the early overdrive pacing in preventing ERAF and/or terminating an AF episode. The EOP effectiveness metric may be defined as the number of times early overdrive pacing has to be terminated in response to (re)detecting an AF episode. For example, the number of times that early overdrive pacing is terminated in response to a sustained AF episode (see blocks 460 and 462 in FIG. 6) may be counted. Alternatively or additionally, the number of times that early overdrive pacing is terminated in response to detecting a new ERAF episode during overdrive pacing may be counted (see blocks 470 and 462 in FIG. 6). Alternatively or additionally, the number of times that early overdrive pacing is delivered for the programmed duration without premature termination due to AF detection may be counted. As such, once early overdrive pacing is enabled in a patient determined to be at risk for ERAF based on the ERAF metric, a separate metric may be monitored to ensure that the early overdrive pacing is effective in reducing the likelihood of ERAF episodes. It is recognized that either or both the ERAF metric and the EOP effectiveness metric may be determined over a floating window of time, for example over the past 24 hours, past week, past month, etc.

The EOP effectiveness metric is compared to a threshold at block 534 to determine if early overdrive pacing is effective in reducing the likelihood of ERAF episodes. A disable threshold may be defined, for example, as a number of times early overdrive pacing is terminated due to detection of a new ERAF episode. If the EOP effectiveness metric meets a predefined disable threshold, as determined at block 534, early overdrive pacing is disabled at block 536.

EXAMPLES

The following examples are intended as illustrative and not limiting embodiments of the disclosed invention.

1. An implantable medical device adapted to prevent an early recurring atrial arrhythmia episode, comprising: a sensing circuit for receiving a cardiac signal; a detection module for detecting an atrial arrhythmia episode from the cardiac signal; a therapy delivery module adapted to deliver an atrial overdrive pacing therapy; and a control module configured to determine if the detected atrial arrhythmia episode is an early recurring episode and enable delivery of the atrial overdrive pacing therapy in response to the detected early recurring atrial arrhythmia.

2. A device according to example 1 wherein the control module being further configured to determine an index corresponding to the early recurring episode, compare the index to a predetermined threshold, and enable delivery of the atrial overdrive pacing therapy in response to the index meeting the predetermined threshold.

3. A device according to example 1 wherein the control module being further configured to commence the atrial overdrive pacing therapy upon detection of one of the atrial arrhythmia episode prior to termination of the atrial arrhythmia episode and a next atrial arrhythmia episode prior to termination of the next atrial arrhythmia episode.

4. A device according to example 1 wherein the control module being further configured to commence the atrial overdrive pacing therapy after detecting an atrial arrhythmia and upon detection of at least one long pause having a predetermined minimum duration.

5. A device according to example 1 wherein determining if the detected atrial arrhythmia episode is an early recurring episode comprises determining if the detecting occurs within a predetermined time subsequent to a previous atrial arrhythmia termination.

6. A device according to example 2 wherein determining the first index comprises determining a duration of the early recurring episode.

7. A device according to example 6 wherein determining the first index further comprises summing the duration of the early recurring episode with a duration of a previously occurring early recurring episode.

8. A device according to example 2 wherein determining the first index comprises determining a second index corresponding to at least one previously occurring atrial arrhythmia episode.

9. A device according to example 8 wherein the at least one previously occurring atrial arrhythmia episode includes an early recurring episode.

10. A device according to example 2 wherein determining the first index comprises determining a frequency of occurrence corresponding to the early recurring episode.

11. A device according to example 1 wherein the therapy delivery module being configured to commence the overdrive pacing therapy in response to detecting one of the atrial arrhythmia episode and a long pause; and wherein the control module being further configured to determine if the atrial arrhythmia episode is terminated after a predetermined interval of time after commencing the overdrive pacing; and terminate the overdrive pacing if the atrial arrhythmia is not terminated.

12. A device according to example 11 wherein the therapy delivery module being configured to deliver the overdrive pacing for a predetermined duration in response to the atrial arrhythmia being terminated.

14. A device according to example 12 wherein the control module being further configured to: detect a new atrial arrhythmia episode after commencing the overdrive pacing; and terminate the overdrive pacing prior to expiration of the predetermined duration in response to detecting the new atrial arrhythmia episode.

15. A device according to example 1 wherein the control module being further configured to determine a metric corresponding to an effectiveness of the overdrive pacing therapy.

16. A device according to example 15 wherein the therapy control module being configured to commence the overdrive pacing therapy for a predetermined interval of time in response to detecting one of an atrial arrhythmia episode and a long pause; terminate the overdrive pacing prior to the predetermined interval of time expiring in response to one of re-detecting the atrial arrhythmia episode and detecting a new atrial arrhythmia episode; wherein the metric corresponding to the effectiveness of the overdrive pacing therapy being one of a number of times overdrive pacing therapy being terminated and a number of times overdrive pacing therapy being delivered for the predetermined interval of time.

17. A device according to example 15 wherein the control module being further configured to disable the overdrive pacing therapy in response to the metric meeting a predetermined disable threshold.

18. An implantable medical device, comprising: means for detecting an atrial arrhythmia episode; means for determining if the atrial arrhythmia episode is an early recurring episode; and means for enabling delivery of an atrial overdrive pacing therapy in response to the early recurring episode.

19. A device according to example 18 further comprising: means for determining a first index corresponding to the early recurring episode; and means for determining if the first index meets a predetermined threshold; wherein the enabling means enables delivery of the atrial overdrive pacing therapy in response to the predetermined threshold being met.

20. A device according to example 18 wherein the means for enabling comprises means for commencing the atrial overdrive pacing therapy at an overdrive pacing rate upon detection of one of the atrial arrhythmia episode prior to termination of the atrial arrhythmia episode and a next atrial arrhythmia episode and prior to termination of the next atrial arrhythmia episode.

21. A device according to example 18 wherein the means for enabling comprises means for commencing the atrial overdrive pacing therapy at an overdrive pacing rate after detecting an atrial arrhythmia episode and upon detection of at least one long pause having a predetermined minimum cycle length interval.

22. A device according to example 18 wherein means for determining if the atrial arrhythmia episode is an early recurring episode comprises means for determining if the detecting occurs within a predetermined time subsequent to a previous atrial arrhythmia termination.

23. A device according to example 19 wherein the means for determining the first index comprises means for determining a duration of the early recurring episode.

24. A device according to example 23 wherein means for determining the first index further comprises means for summing the duration of the early recurring episode with a duration of a previously detected early recurring episode.

25. A device according to example 19 wherein the means for determining the first index comprises means for determining a second index corresponding to at least one previously occurring atrial arrhythmia episode.

26. A device according to example 25 wherein the at least one previously occurring atrial arrhythmia episode includes an early recurring episode.

27. A device according to example 19 wherein the means for determining the first index comprises means for determining a frequency of occurrence corresponding to the early recurring episode.

28. A device according to example 18 further comprising: means for commencing the overdrive pacing therapy in response to detecting one of the atrial arrhythmia episode and a long pause; means for determining if the atrial arrhythmia episode is terminated after a predetermined interval of time after commencing the overdrive pacing; and means for terminating the overdrive pacing if the atrial arrhythmia is not terminated.

29. A device according to example 28 further comprising means for delivering the overdrive pacing for a predetermined duration in response to the atrial arrhythmia being terminated.

30. A device according to example 29 further comprising: means for detecting a new atrial arrhythmia episode after commencing the overdrive pacing; and means for terminating the overdrive pacing prior to expiration of the predetermined duration in response to detecting the new atrial arrhythmia episode.

31. A device according to example 18 further comprising means for determining a metric corresponding to an effectiveness of the overdrive pacing therapy.

32. A device according to example 31 further comprising: means for commencing the overdrive pacing therapy for a predetermined interval of time in response to one of an atrial arrhythmia episode and a long pause; and means for terminating the overdrive pacing therapy prior to the predetermined interval of time expiring in response to one of re-detecting the atrial arrhythmia episode and detecting a new atrial arrhythmia episode; wherein the metric corresponding to the effectiveness of the overdrive pacing therapy being one of a number of times overdrive pacing being terminated and a number of times overdrive pacing being delivered for the predetermined interval of time.

33. A device according to example 31 further comprising disabling the overdrive pacing therapy in response to the metric meeting a predetermined disable threshold.

Thus, an IMD and associated method for controlling atrial overdrive pacing have been presented in the foregoing description with reference to specific embodiments. It is appreciated that various modifications to the referenced embodiments may be made without departing from the scope of the invention as set forth in the following claims.

The invention claimed is:

1. A method performed by an implantable medical device, comprising:
   detecting atrial arrhythmia episodes;
   determining if a detected atrial arrhythmia episode is an early recurring episode;
   determining a first index corresponding to the early recurring atrial arrhythmia episode in response to determining the atrial arrhythmia episode is an early recurring episode;
   determining whether the first index meets a predetermined threshold; and
   enabling delivery by the implantable medical device of an atrial overdrive pacing therapy following detection of and prior to termination of a detected atrial arrhythmia in response to the predetermined threshold being met.

2. A method according to claim 1 wherein the delivery of atrial overdrive pacing therapy comprises commencing the atrial overdrive pacing therapy at an overdrive pacing rate responsive to detecting an atrial arrhythmia episode and at least one long pause having at least a predetermined minimum cycle length duration.

3. A method according to claim 1 wherein determining if the atrial arrhythmia episode is an early recurring episode comprises determining if the detecting occurs within a predetermined time subsequent to a previous atrial arrhythmia termination.

4. A method according to claim 1 wherein determining the first index comprises determining a duration of the early recurring episode.

5. A method according to claim 1 wherein determining the first index comprises determining a second index corresponding to at least one previously occurring atrial arrhythmia episode.

6. A method according to claim 5 wherein the at least one previously occurring atrial arrhythmia episode includes an early recurring episode.

7. A method according to claim 1 wherein determining the first index comprises determining a frequency of occurrence corresponding to the early recurring episode.

8. A method according to claim 1 further comprising:
   commencing the overdrive pacing therapy in response to detecting the atrial arrhythmia episode and a long pause;
   determining if the atrial arrhythmia episode is terminated after a predetermined interval of time after commencing the overdrive pacing; and
   terminating the overdrive pacing if the atrial arrhythmia is not terminated.

9. A method according to claim 8 further comprising delivering the overdrive pacing for a predetermined duration in response to the atrial arrhythmia being terminated.

10. A method according to claim 9 further comprising:
    detecting a new atrial arrhythmia episode after commencing the overdrive pacing; and terminating the overdrive pacing prior to expiration of the predetermined duration in response to detecting the new atrial arrhythmia episode.

11. A method according to claim 1 further comprising determining a metric corresponding to an effectiveness of the overdrive pacing therapy.

12. A method according to claim 11 further comprising:
commencing the overdrive pacing therapy for a predetermined interval of time in response to the atrial arrhythmia episode and a long pause; and
terminating the overdrive pacing therapy prior to the predetermined interval of time expiring in response to one of re-detecting the atrial arrhythmia episode and detecting a new atrial arrhythmia episode;
wherein the metric corresponding to the effectiveness of the overdrive pacing therapy being one of a number of times overdrive pacing being terminated and a number of times overdrive pacing being delivered for the predetermined interval of time.

13. A method according to claim 11 further comprising disabling the overdrive pacing therapy in response to the metric meeting a predetermined disable threshold.

14. A method according to claim 1 wherein the delivery of atrial overdrive pacing therapy comprises commencing the atrial overdrive pacing therapy responsive to detection of one of the atrial arrhythmia episode determined to be an early recurring episode or a next atrial arrhythmia episode.

15. A method performed by an implantable medical device, comprising:
detecting an atrial arrhythmia episode;
determining if the atrial arrhythmia episode is an early recurring episode;
determining a first index corresponding to the early recurring atrial arrhythmia episode in response to determining the atrial arrhythmia episode is an early recurring episode;
determining whether the first index meets a predetermined threshold; and enabling delivery by the implantable medical device of an atrial overdrive pacing therapy in response to the predetermined threshold being met;
wherein determining the first index comprises determining a duration of the early recurring episode; and
wherein determining the first index further comprises summing the duration of the early recurring episode with a duration of a previously detected early recurring episode.

16. A non-transitory computer-readable medium having computer-executable instructions executable by an implantable medical device for: detecting atrial arrhythmia episodes; determining if a detected atrial arrhythmia episode is an early recurring episode; determining a first index corresponding to the early recurring atrial arrhythmia episode in response to determining the atrial arrhythmia episode is an early recurring episode; determining whether the first index meets a predetermined threshold; and enabling delivery by the implantable medical device of an atrial overdrive pacing therapy following detection of and prior to termination of a detected atrial arrhythmia in response to the predetermined threshold being met.

17. The medium of claim 16 wherein delivery of the atrial overdrive pacing therapy comprises commencing the atrial overdrive pacing therapy responsive to detecting the atrial arrhythmia episode and at least one long pause having a predetermined minimum cycle length duration.

18. The medium of claim 16 wherein determining if the atrial arrhythmia episode is an early recurring episode comprises determining if the detecting occurs within a predetermined time subsequent to a previous atrial arrhythmia termination.

19. The medium of claim 16 wherein determining the first index comprises determining a duration of the early recurring episode.

20. The medium of claim 16 wherein determining the first index comprises determining a second index corresponding to at least one previously detected atrial arrhythmia episode.

21. The medium of claim 20 wherein the at least one previously occurring atrial arrhythmia episode includes an early recurring episode.

22. The medium of claim 16 wherein determining the first index comprises determining a frequency of occurrence corresponding to the early recurring episode.

23. The medium of claim 16 wherein delivery of the atrial overdrive pacing therapy comprises commencing the atrial overdrive pacing therapy responsive to detection of one of the atrial arrhythmia episode determined to be an early recurring episode or a next atrial arrhythmia episode.

24. A non-transitory computer-readable medium having computer-executable instructions executable by an implantable medical device for detecting an atrial arrhythmia episode; determining if a detected atrial arrhythmia episode is an early recurring episode; determining a first index corresponding to the early recurring atrial arrhythmia episode in response to determining the atrial arrhythmia episode is an early recurring episode; determining whether the first index meets a predetermined threshold; wherein determining the first index comprises determining a duration of the early recurring episode; and wherein determining the first index further comprises summing the duration of the early recurring episode with a duration of a previously detected early recurring episode.

* * * * *